US009320283B2

(12) United States Patent
Widmer et al.

(10) Patent No.: US 9,320,283 B2
(45) Date of Patent: Apr. 26, 2016

(54) ***TRICHODERMA ASPERELLUM* TO REMEDIATE *PHYTOPHTHORA RAMORUM*-INFESTED SOIL**

(71) Applicant: The United States of America, as represented by the Secretary of Agriculture, Washington, DC (US)

(72) Inventors: Timothy L. Widmer, Frederick, MD (US); Gary J. Samuels, Deering, NH (US)

(73) Assignee: The United States of America, as repressented by The Secretary of Agriculture, Washington, DC (US)

( * ) Notice: Subject to any disclaimer, the term of this patent is extended or adjusted under 35 U.S.C. 154(b) by 0 days.

(21) Appl. No.: 13/971,294

(22) Filed: Aug. 20, 2013

(65) Prior Publication Data

US 2015/0056169 A1 Feb. 26, 2015

(51) Int. Cl.
*A01N 63/04* (2006.01)
*C12R 1/885* (2006.01)

(52) U.S. Cl.
CPC ................ *A01N 63/04* (2013.01); *C12R 1/885* (2013.01)

(58) Field of Classification Search
IPC ................................. A01N 63/04; C12R 1/885
See application file for complete search history.

(56) References Cited

FOREIGN PATENT DOCUMENTS

JP 2006199601 A * 8/2006

OTHER PUBLICATIONS

English machine translation of National Agricultural and Food Research Organization (Dokuritsu Gyosei Hojin Nogyo Seibutsu SH) and Kankyo Eng KK, JP 2006-199601 A, translated on the Japanese Pat. Office website, http://www19.ipdl.inpit.go.jp/PA1/cgi-bin/PA1INIT?1413897259747, on Oct. 17, 2014.*

English abstract of National Agricultural and Food Research Organization (Dokuritsu Gyosei Hojin Nogyo Seibutsu SH) and Kankyo Eng KK, JP 2006-199601 A.*

Chung, Y.R. et al., Interactions Between Thermophilic Fung and *Trichoderma hamatum* in Suppression of Rhizoctonia Damping-Off in a Bark Compost-Amended Container Medium, The American Phytopathological Society, 1990, pp. 73-77, vol. 80 (1).

Gupta, V.P. et al., Ultrastructure of Mycoparasitism of *Trichoderma, Gliocladium* and *Laetisaria* Species on Botryodiplodia Theobromae, J. Phytopathology, 1999, pp. 19-24, vol. 147.

(Continued)

*Primary Examiner* — Rosanne Kosson
(74) *Attorney, Agent, or Firm* — John D. Fado; Evelyn M. Rabin

(57) ABSTRACT

Despite efforts of eradication and sanitation, *Phytophthora ramorum* persists in the United States and has been a problem in commercial nurseries since 2001. Detection in a nursery immediately causes the nursery to be under quarantine until the *P. ramorum* can be proven to be eradicated. Treatment with the biological control agent *Trichoderma asperellum* showed promise in laboratory results to remediate *P. ramorum*-infested potting soil. Sixteen *T. asperellum* isolates were screened, found to have variable mycoparasitic activities, and further tested in natural field settings. Field plots having *P. ramorum*-infested soil were treated with *T. asperellum*, a chemical and two different commercial biological control products and compared to non-treated infested soil. After 8 weeks, *P. ramorum* populations were not detected in the soil treated with *T. asperellum* isolate 04-22 showing that *T. asperellum* isolate 04-22 could remediate soils infested with *P. ramorum* under natural field conditions.

8 Claims, 5 Drawing Sheets
(2 of 5 Drawing Sheet(s) Filed in Color)

(56) References Cited

OTHER PUBLICATIONS

Harman, G.E. et al., *Trichoderma* Species—Opportunistic, Avirulent Plant Symbionts, Nature Reviews Microbiology, 2004, pp. 43-56, vol. 2.

Heungens, K. et al., Within-Field Spread of *Phytophthora ramorum* on Rhododendron in Nursery Settings, Proceedings of the Sudden Oak Death Fourth Science Symposium, 2010, pp. 72-75.General Technical Report PSW-GTR-229.

Hoitink, Haj et al., Biocontrol Within the Context of Soil Microbial Communities: A Substrate-Dependent Phenomenon, Annu. Rev. Phytopathol., 1999, pp. 427-446, vol. 37.

Smith, V.L. et al., Potential for Biological Control of *Phytophthora* Root and Crown Rots of Apple by *Trichoderma* and *Gliocladium* spp., Phytopathology, 1990, pp. 880-885, vol. 80 (9).

Tehrani, A.S. et al., Antagonistic Effects of *Trichoderma harzianum* on *Phytophthora dreschsleri*, the Casual Agent of Cucumber Damping-Off, Acta Hort., 2004, pp. 137-139, vol. 635.

Watanabe, S. et al., Mode of Action of *Trichoderma asperellum* SKT-1, a Biocontrol Agent Against Gibberella Fujikuroi, J. Pestic. Sci., 2007, pp. 222-228, vol. 32 (3).

Widmer, T.L. et al., Screening *Trichoderma asperellum* as a Mycoparasite on *Phytophthora ramorum*, Proceedings of Sudden Oak Death Fourth Science Symposium, 2010, pp. 375-378, General Technical Report PSW-GTR-229.

\* cited by examiner

TRICHODERMA ASPERELLUM TO REMEDIATE PHYTOPHTHORA RAMORUM-INFESTED SOIL

BACKGROUND OF THE INVENTION

1. Field of the Invention

This invention relates to identifying particular *Trichoderma asperellum* isolates as biocontrol agents and their use for reducing *Phytophthora ramorum* growth in soil, for the remediation of *P. ramorum*-infested soil in commercial nurseries, and for the protection of potted, rooted plants from infestation and spread of *P. ramorum*. The *T. asperellum* isolates control soilborne plant disease by reducing *P. ramorum* populations and suppressing the spread and reemergence of *P. ramorum* in the soil. The invention relates to particular *T. asperellum* isolates screened for their mycoparasitic characteristics and effective antagonistic activity for *P. ramorum*. The present invention relates to a biocontrol method comprising the application of a particular *T. asperellum* isolate to soil infested with *P. ramorum*, such as commercial nursery soil, to obtain remediated soil, i.e., soil where *P. ramorum* is not detectable. Potting soil amended with *T. asperellum* isolate 04-22 protects uninfected plants from *P. ramorum* infestation and suppresses sporulation and further infection of *P. ramorum* infested plants.

2. Description of the Relevant Art

*Phytophthora ramorum* Werres, de Cock, and Man in't Veld, causal agent of sudden oak death (SOD) and *ramorum* blight, is a pathogen of worldwide concern. *Phytophthora ramorum* is known to have broad host range based upon isolations from natural and artificial laboratory infections (USDA/APHIS. 2012. Retrieved from the Internet Mar. 18, 2013: <URL: aphis.usda.gov/plant_health/plant_pest_info/pram/downloads/pdf_files/usdaprlist.pdf). In the United States, where it is a regulated quarantine organism, *P. ramorum* has a limited distribution in forests in coastal California and Oregon. *P. ramorum* was first confirmed in a US nursery in 2001 in Santa Cruz County, Calif. (Frankel, S. J. 2008. *Austral. Plant Path.* 37:19-25). Despite regulations on the movement of *P. ramorum* host material from known infested Californian counties, the pathogen was detected in 20 different states by the end of 2004 (Cooperative Agriculture Pest Survey Program. 2005. *Phytophthora ramorum* 2004 *National Nursery Survey*. USDA-APHIS, Plant Protection and Quarantine. 15 pp.). To date, on the east coast, *P. ramorum* has only been isolated from nursery sites (and in a few instances, from residential sites where infected nursery stock had been planted) and from adjacent bodies of water (Cave et al. 2008. Retrieved from the Internet Mar. 18, 2013: <URL: aphis.usda.gov/plant_health/plant_pest_info/pracphst-08.pdf; Jeffers et al. 2010. In: *Proceedings of the Sudden Oak Death Third Science Symposium*, eds. Frankel et al., General Technical Report PSW-GTR-229, Albany, Calif.: Pacific Southwest Research Station, Forest Service, USDA, pp. 69-71). However, there are many susceptible forest hosts, leading to a high potential for spread to forested areas.

*Ramorum* blight, the disease of ornamental plants caused by *P. ramorum*, is considered to have only a moderate impact on ornamental plants since it is usually not lethal to these hosts (Kliejunas, J. T. 2011. In: *A Risk Assessment of Climate Change and the Impact of Forest Diseases on Forest Ecosystems in the Western United States and Canada*. General Technical Report PSW-GTR-235, Albany, Calif.: Pacific Southwest Research Station, Forest Service, USDA). Symptoms on rhododendrons, camellias, viburnums, and other hosts are usually non-distinctive leaf necrosis and blights that are not easily distinguishable from other diseases. However, more importantly, *ramorum* blight has a serious impact on the nursery industry. The continued detections of *P. ramorum* on ornamental nursery stock (Tubajika et al. 2006. *Plant Health Progress* doi: 10.1094/PHP-2006-0315-02-RS) has increased concern about the potential spread of this pathogen throughout the nursery industry. Because long distance dispersal of *P. ramorum* is facilitated by shipments of infected nursery plants across the country (Parke and Lucas. 2008. Retrieved from the Internet Sep. 6, 2012: <URL: The Plant Health Instructor. Doi: 10.1094/PHI-I-2008-0227-01) and because concerns exist that the pathogen could spread from nurseries into natural habitats (Davidson et al. 2005. *Phytopath.* 95:587-596), strict guidelines have been imposed on nurseries in areas known to have *P. ramorum*. These restrictions have had substantial economic consequences for the nursery industry (Kliejunas, supra).

Once *P. ramorum* is detected in a nursery, a set of procedures (the APHIS Confirmed Nursery Protocol) must be carried out to eradicate the pathogen (USDA/APHIS. 2005. Retrieved from the Internet: <URL: aphis.usda.gov/plant_health/plant_pest_info/pram/downloads/pdf_files/CNPv7.pdf). However, remediation of infested nurseries has proved problematic. There have been recurrent infections of plants in nurseries where diseased plants were detected and removed. In 2005, the California Department of Food and Agriculture identified 53 *P. ramorum*-positive California nurseries, eight of which had recurrent infections; in 2006, 24 recurrent nurseries were reported; in 2007, five were reported (California Oak Mortality Task Force [COMFT], 2009. Retrieved from the Internet April, 2009: <URL: nature.berkeley.edu/comtf/html/chronology.htm). It was not always clear if the recurrence was due to a new introduction of diseased stock, or to infection of healthy plants from some source of inoculum persisting in the nursery.

Studies have shown that *P. ramorum* has a soilborne phase and can persist in soil and potting mix, thus playing an important role in survival and infection of new hosts (Shishkoff, N. 2007. *Plant Dis.* 91:1245-1249; Linderman and Davis. 2006. *HortTech.* 16:502-507). Resistant spores, such as *P. ramorum* chlamydospores, can survive in soil for long periods of time (Erwin and Ribeiro. 1996. *Phytophthora Diseases Worldwide*. APS Press, St. Paul, Minn.). The pathogen has been recovered from the soil directly below containerized plants (Jeffers, S. 2005. *Phytopath.* 95: S48; Tjosvold at al. 2009. *Plant Disease* 93:371-376; Dart et al. 2007. *Plant Dis.* 91:1419-1422), from litter on the ground (Neubauer at al. 2006. *Gesunde Pflanzen* 58:185-191), as well as from the rootball of an asymptomatic non-host plant (Dart and Chastagner. 2007. Retrieved from the Internet: Plant Health Progress doi:10.1094/PHP-2007-0816-01-BR). Further, *P. ramorum* was found not to be limited to the organic layer of soil, as it has been detected in 10-cm deep soil samples (Dart at al., supra). The continuing spread and reemergence of *P. ramorum* from infested nursery stock has emphasized the difficulty in eliminating this pathogen completely with current management practices such as treating with metam-sodium, attempting eradication, removing large quantities of soil, or shutting down the nursery completely (Frankel, supra; Yakabe and MacDonald. 2008. In: *Proceedings of the Sudden Oak Death Third Science Symposium*, eds. Frankel et al., General Technical Report PSW-GTR-214, Albany, Calif.: Pacific Southwest Research Station, Forest Service, USDA, pp. 113-114).

In order to remove restrictions on individual nurseries, these establishments must prove that they no longer have *P. ramorum* by testing the soil and plant material (USDA/

APHIS. 2010. Retrieved from the Internet Sep. 6, 2012: <URL: aphis.usda.gov/plant_health/plant_pest_info/pram/downloads/CNP/CNP %20v8.0%201-2011.pdf). If *P. ramorum*-infected plant material is found, the required protocol dictates that all host and associated host plants within a defined destruction block be destroyed (USDA/APHIS 2010, supra). In addition, a 10-meter radius around the destruction block is designated as a quarantine block, where plants cannot be moved in or out, and must be maintained in that status for a minimum period of 90 days to determine if *P. ramorum* has spread beyond the border of the destruction block. Ornamental plants often are cultivated under high density conditions that could easily facilitate plant-to-plant spread of *P. ramorum* outside the initial destruction block (Englander and Tooley. 2003. Retrieved from the Internet Sep. 6, 2012: <URL:apsnet.org/online/SOD.doi: 10.1094/SOD-2003-LE). *P. ramorum* has been demonstrated to spread plant-to-plant in aerial infections by physical contact and splash from rain and overhead irrigation with symptoms often taking some time to be noticed (Heungens et al. 2010. In: *Proceedings of the Sudden Oak Death Fourth Science Symposium*, eds. Frankel et al., General Technical Report PSW-229, Albany, Calif.: Pacific Southwest Research Station, Forest Service, USDA, pp. 72-75; Tjosvold et al. 2008. Retrieved from the Internet Sep. 6, 2012: <URL: *Plant Health Progress*. Doi:10.1094/PHP-2008-01-RS).

Different techniques, such as pressure washing or chemical sanitization, are used by growers to attempt to decontaminate used containers. Aerated steam and chemical fumigants are known methods to eliminate soilborne pathogens. Linderman and Davis (2008a. *HortTech*. 18:106-110) found that *P. ramorum* populations in potting media were killed by aerated steam heat treatments of 50° C. or higher or treatment with metam sodium concentrations of 0.25 ml per liter of medium. However, using these techniques increases the chance of destroying beneficial microorganisms and of working in a hazardous environment.

It is essential to controlling the spread of this pathogen that infested nurseries be successfully cleaned of all propagules of the pathogen. Although remediation studies using chemical sterilants have been done in situ in infested nurseries in California (Yakabe and MacDonald, supra), there was no opportunity at that time to set up control plots where soil was left untreated; therefore, it was difficult to evaluate efficacy of the treatments. In addition, chemical sterilants, while often effective, have limitations because of their toxicity; many cannot be used in residential areas. Therefore, safer alternatives would be a necessary addition to the list of possible control measures in a good integrated pest management system.

There have been numerous studies examining the use of fungicides to control *P. ramorum* on ornamentals (Heungens et al. 2006. In: *Proceedings of the Sudden Oak Death Second Science Symposium*, eds. Frankel et al., General Technical Report PSW-196, Albany, Calif.: Pacific Southwest Research Station, Forest Service, USDA, pp. 241-257; Linderman and Davis. 2008b. *Plant Health Progress*. Doi:10.1094/PHP-2008-2011-01-RS; Tjosvold at al. 2008, supra; Pérez-Sierra et al. 2011. *Plant Path*. 60:1069-1076). Although fungicides are effective to some degree when applied as a preventative (Heungens at al. 2006, supra; Tjosvold et al. 2008, supra), they require repeated applications. Linderman and Davis (2008b, supra) found that all chemicals tested in their study were fungistatic and not fungicidal. Besides environmental concerns, repeated applications potentially could lead to fungicide resistance by the pathogen as has been observed by other *Phytophthora* spp. (Grünwald at al. 2006. *Phytopath*. 96:1397-1403). In addition, U.S. and European Union regulations prohibit the application of fungicides in the quarantine zones (USDA/APHIS 2010, supra; Pérez-Sierra et al., supra) due to potential masking of symptoms. These concerns have lead to the desire to investigate other control options, including biological control.

Biological control through the use of microorganisms is a method to manage plant diseases that has gained a lot of interest due to its sustainability and low negative impacts on the environment. In natural soil, oomycetes, chytrids, actinomycetes, hyphomycetes, and bacteria were observed to parasitize oospores of different *Phytophthora* spp. (Sneh at al. 1977. *Phytopath*. 67:622-628). Some of the most studied and promising fungi used in a biocontrol system are *Trichoderma* spp. (Harman at 2004. *Nature Rev. Microbiol*. 2:43-56; Smith at al. 1990. *Phytopath*. 70:880-885).

Populations of *Trichoderma* spp., which are often abundant in composts and compost-amended media, typically suppress *Pythium* and *Phytophthora* root rots within days after their formulation (De Ceuster and Hoitink. 1999. *Compost Sci. Util*. 7:6-15.; Hoitink and Boehm. 1999. *Ann. Rev. Phytopath*. 37:427-446). *Trichoderma* spp. are reported to suppress soilborne diseases caused by *Rhizoctonia solani* Kuhn and *Phytophthora* spp. in containerized systems (Chung and Hoitink. 1990. *Phytopath*. 80:73-77; da S. Costa at al. 2000. Brazilian *J. Microbiol*. 31:239-246; Sharifi Tehrani and Nazari. 2004. *Acta Horticulturae* 635:137-139). *Phytophthora capsici* populations were reduced when infested soil was amended with *T. harzianum* (Ezziyyani at al. 2007. *J. Phytopath*. 155:342-349; Sid Ahmed et al. 1999. *Plant Path*. 48:58-65). Mycoparasitism by the *Trichoderma* spp. was shown to be the primary mode of action that reduced populations of various pathogenic soil fungi (Gupta et al. 1999. *J. Phytopath*. 147:19-24; Watanabe et al. 2007. *J. Pesticide Sci*. 32:222-228). Currently, *T. asperellum* is being studied as a biological control agent to manage black pod disease of cacao in Cameroon. Recent results show that disease incidence was lower when *T. asperellum* was applied on infected cacao trees (Tondje et al. 2007. *Biol. Control*. 43:202-212).

While these various biocontrol methods and formulations for effective control of plant diseases, including those diseases caused by *Phytophthora*, are known in the art, there still remains a need for effective biocontrol agents for controlling *P. ramorum* populations and for suppressing the spread of *P. ramorum*-contaminated soil to nurseries and non-commercial areas such as residential and forested soil so that drastic measures such as repeated destruction of plants, removal of large quantities of soil or complete closure of nursery locations are not employed. The present invention, described below, provides a particular, effective *Tricoderma asperellum* isolate and methods of using this isolate to effectively remediate *P. ramorum*-infested soil and to protect potted, rooted plants from infection and spread of *P. ramorum*.

SUMMARY OF THE INVENTION

We have identified a particular *T. asperellum* isolate and discovered that this *T. asperellum* isolate can suppress *P. ramorum* populations in the soil and prevent the spread and reemergence of *P. ramorum*, resulting in remediation of large areas of previously infested soil where *P. ramorum* is not detectable.

In accordance with this discovery, it is an object of the invention to provide *T. asperellum* isolates which can act as biocontrol agents and suppress soil infestation by *P. ramorum*.

It is a further object of the invention to provide a biocontrol composition for reducing *P. ramorum* populations in the soil wherein said composition comprises a *T. asperellum* isolate as a biocontrol agent wherein said *T. asperellum* isolate is 04-22.

It is an additional object of the invention to provide a biocontrol method of suppressing *P. ramorum* infestation of nursery soil which includes applying a *T. asperellum* isolate as a biocontrol agent to control *P. ramorum* and to suppress *P. ramorum* to undetectable levels.

It is an another object of the invention to provide a biocontrol method for remediating nursery soil infested with *P. ramorum* which includes applying a *T. asperellum* isolate as a biocontrol agent to the *P. ramorum*-infested soil and obtaining soil where *P. ramorum* is not detectable.

It is an additional object of the invention to provide a biocontrol method for protecting or preventing potted rooted plants from infection and spread of *P. ramorum*.

Also part of this invention is a kit, comprising a biocontrol composition for application to soil to suppress *P. ramorum* contamination and prevent the spread and reemergence of *P. ramorum*.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 1A shows a colonized strip of *Trichoderma* spp. overlaid on V8 agar colonized by *Phytophthora ramorum*. FIG. 1B depicts a 1 cm by 4.5 cm strip removed, divided in half and cut into nine 0.5 cm plugs every week. FIG. 1C shows the 0.5 cm plugs placed on *Rhododendron* "Cunningham's White" leaf disks. FIG. 1D shows the 0.5 cm plugs placed on V8 agar supplemented with benomyl.

DETAILED DESCRIPTION OF THE INVENTION

Figure 1:
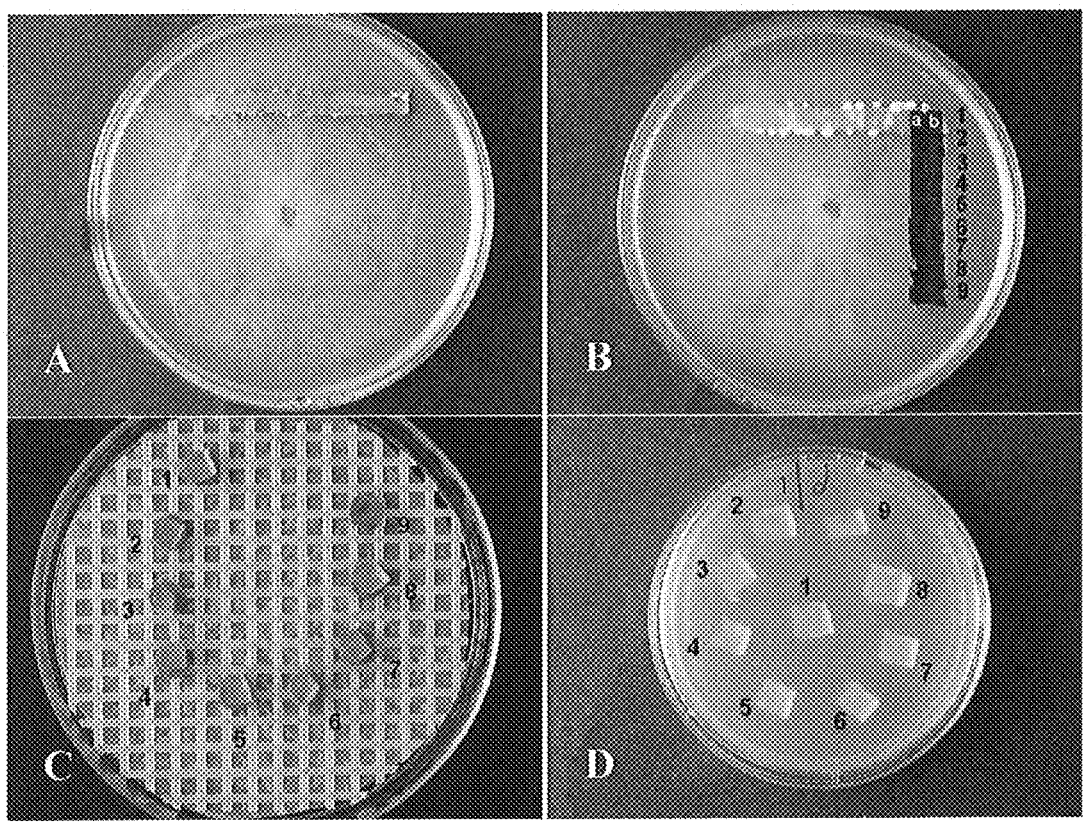
FIGS. 1A-1D depict stages of the Dual Culture Bioassay.

We have identified an isolate of *Trichoderma* spp. that is effective for suppressing *P. ramorum* infestation of soil preventing further spread and reemergence of the *P. ramorum* and also effective for protecting potted, rooted plants from infestation by *P. ramorum* by amending potting soil with *T. asperellum* isolate 04-22. Preliminary results in our laboratory had demonstrated that specific *Trichoderma* spp. isolates were effective in parasitizing *P. ramorum* chlamydospores (Widmer and Samuels. 2010. In: *Proceedings of the Sudden Oak Death Fourth Science Symposium*, eds. Frankel et al., General Technical Report PSW-229, Albany, Calif.: Pacific Southwest Research Station, Forest Service, USDA, pp. 375-378).

Further, preliminary tests conducted under laboratory conditions have demonstrated that various isolates of *T. asperellum* have reduced high populations of *P. ramorum* (>150 chlamydospores per $cm^3$ soil) to non-detectable limits after 2 to 4 weeks. In a replicated trial, *T. asperellum* isolate 04-22 reduced a *P. ramorum*-infested potting mix to near non-detectable limits after 3 weeks when incorporated at a rate of $1 \times 10^7$ $CFU/cm^3$ medium at 20° C. (Widmer, unpublished).

Large quantities of the selected *Trichoderma* spp. isolates were expanded on rice grains and the amount of colony forming units (CFU) present were determined (as shown in Example 1). The expanded *Trichoderma* spp. isolates were tested in a dual culture bioassay for antagonistic activity against three isolates of *P. ramorum* (Example 2). Under these laboratory conditions, the *T. asperellum* isolates 04-22, 07-66, 06-287, 01-294, 06-283, 02-64 and 02-65 showed consistent antagonism of *P. ramorum*.

These *T. asperellum* isolates were further tested in a soil bioassay (Example 3) where the *T. asperellum* isolates, expanded on autoclaved rice and *P. ramorum* chlamydospores distributed in sand were cultured together. Aliquots were removed weekly to determine the effect of the *T. asperellum* isolates on the *P. ramorum* population. The presence of the *T. asperellum* isolates 04-22 and 02-64, in particular, significantly reduced the *P. ramorum* population. In this soil bioassay, the other *T. asperellum* isolates did not significantly or consistently decrease *P. ramorum* populations.

The *T. asperellum* isolate 04-22 was further tested in field studies. Isolate 04-22 was grown under large scale conditions on wheat bran (Example 4). Large quantities of *P. ramorum* were prepared for use as soil inoculants in the field plots. The National Ornamentals Research Site, Dominican University of California, San Rafael, Calif., located in a *P. ramorum*-infested county was selected as Study Site One. The field study was structured in a completely randomized split-plot design, comprising microplots. Each microplot was randomly assigned one of the following treatments: (1) Non-treated control; (2) Subdue GR® (Mefenoxam, Syngenta Crop Protection, Inc., Greensboro, N.C.); (3) *Trichoderma asperellum* isolate 04-22 grown on wheat bran as described above; (4) RootShield® (*Trichoderma harzianum* strain T-22, BioWorks, Inc., Victor, N.Y.); and (5) SoilGard® (*Gliocladium virens* GL-21, Certis USA, Columbia, Md.). The experiment was conducted during the fall and the following spring.

The soil within each microplot was artificially infested with an amount of the *P. ramorum*-infested sand, so that the intended initial population of *P. ramorum* was approximately 30 propagules/$cm^3$. Soil infestation was done by evenly distributing an aliquot of *P. ramorum* chlamydospores-infested sand over the soil and raking it in. The plot was watered to settle the surface. After a one week period to allow for stabilization of the *P. ramorum* population, ten soil samples were collected within each microplot in randomized areas throughout the microplot. The subsamples from each microplot were combined and sampled for *P. ramorum* and *Trichoderma* spp. populations.

Each microplot was then treated with one of the following designated treatments: Subdue® GR (Mefenoxam, a chemical treatment), *T. asperellum*, isolate 04-22, RootShield® (*Trichoderma harzianum* strain T-22), and SoilGard® (*Gliocladium virens* GL-21). After 2, 4, 8 and 12 weeks, ten soil subsamples were taken from each microplot and combined. After the last samples were taken at 12 weeks, the microplots and the soil were disinfected with steam via a steam, generator. The plot was prepared and established again for the spring trial as described above. The experiment was repeated the following year.

*P. ramorum* and *Trichoderma* spp. soil populations of the microplots were quantified by the soil dilution plating method. Detectable levels of *P. ramorum* populations differed in the fall and spring trials. In the fall applications, *P. ramorum* populations increased in the non-treated control and RootShield®-treated microplots after 2 weeks and then declined over time, although always maintaining a detectable level up to the final sampling time of 12 weeks. The *P. ramorum* population in the chemical-treated microplots immediately fell to non-detectable levels, but was detected again after 4 and 8 weeks. Populations of *P. ramorum* in the *T. asperellum*- and SoilGard®-treated microplots started to decline immediately. *P. ramorum* was detected in some of the microplots treated with SoilGard®; but, some had non-detectable levels. *P. ramorum* was not detected after 8 weeks in the *T. asperellum*-treated microplots and remained at non-detectable levels up to the last sampling time. In the spring application, *P. ramorum* populations immediately declined in all treatments. However, after 8 and 12 weeks, *P. ramorum* populations were not detectable only in the *T. asperellum*- and chemical-treated microplots. Other treatment groups returned to detectable levels.

A commercial nursery in the San Joaquin Valley, Calif. that had tested positive for *P. ramorum* in the soil from samples collected by State Regulators was selected as Study Site 2 of the field trials. Plot size set for treatment was 3.7 m by 4.6 m. Half of the plot was rototilled to a depth of 2 cm, and wheat bran, colonized by *T. asperellum*, was distributed as evenly as possible over the entire plot. The total amount of *T. asperellum* added to the plot was $6.74 \times 10^{11}$ CFU, which was 2600 g of wheat bran. The wheat bran was raked into the soil and the soil was initially hand watered to settle the plot and watered when necessary by overhead irrigation to maintain moisture in the soil. Another plot, 3.5 by 4 m in size, and approximately 15 m from the treated plot, was left untreated as a control and maintained as described above.

Soil samples were collected from six locations throughout the treated (half were in the rototilled section) and non-treated plot prior to the application of the colonized wheat bran and 5 weeks after application. The samples were analyzed in the leaf disk assay using leaves of *Rhododendron* 'Cunningham's White' (Example 5). *P. ramorum* was detected in the soil prior to the treatment. Five weeks after the application of *T. asperellum, P. ramorum* was not detected in the collected soil samples from the treated plot, regardless of whether the plot was rototilled or not. These results were confirmed California Department of Food and Agriculture (CDFA); USDA/APHIS-PPQ released the nursery from quarantine status. Thus, *T. asperellum* could remediate soil infested with *P. ramorum* under natural field conditions.

Protection of plant roots of *Viburnum tinus* from infection by *P. ramorum* was evaluated in a trial where potting mix was amended with *T. asperellum*, isolate 04-22, grown on wheat bran as described in Example 3 and the field studies of Example 4, so that the final concentrations were $1 \times 10^5$, $1 \times 10^6$, and $1 \times 10^7$, CFU/cm$^3$ of potting mix in bags 1, 2, and 3, respectively, and a fourth bag was left non-amended as a control. Twenty-four rooted *V. tinus* cuttings were transplanted into square plastic pots containing amended or non-amended potting mix. The pots were placed on a greenhouse bench with drip irrigation. One week later, the *V. tinus* cuttings were inoculated with *P. ramorum* by drenching the soil in each pot with a suspension of either chlamydospores or sporangia. The pots were maintained on the greenhouse bench with drip irrigation for 3 weeks, the cuttings were removed from the soil and the stem cut at the soil line. The roots were observed for *P. ramorum* mycelium growth into the agar medium after 1 week. Results clearly showed that *T. asperellum* affords protection of the roots from infection of *P. ramorum*. In the non-amended potting soil control group, 75% of the plants showed some infection of *P. ramorum* on the roots. However, as the concentrations of *T. asperellum* increased, a correlation with root protection was observed. At the $10^5$, $10^6$, and $10^7$ concentrations, only 42%, 33%, and 25% of the plants in the *T. asperellum*-amended potting mix showed infection, respectively. Thus, preventing infection of the roots of plants planted in potting soil is not only beneficial to the individual plant but the decrease in *P. ramorum* infection also helps to diminish the spread of *P. ramorum* infestation into the environment.

The suppression of sporulation of *P. ramorum* on *V. tinus* plant roots was tested using an assay which quantifies *P. ramorum* inoculum in runoff. Twelve plants transplanted in Turface were inoculated by pouring a sporangial suspension over each root system established in Turface and allowing 24 hr for infection. Four control plants were treated with water alone. Plants were then removed from the infested or noninfested (control) Turface and the roots carefully washed to remove all Turface granules (and any residual inoculum from infested plants). Plants were then transplanted into plastic pots containing approximately 100 ml of clean Turface and kept in a controlled-environment chamber set at 20° C. with a 14-hr photoperiod. Three days after transplanting, six of the inoculated plants and two of the controls were treated with a top-dressing of wheat bran infested with *T. asperellum*. Runoff was sampled at 7, 14, 21, 28 and 35 days after inoculation (see Example 6). Sporulation of *P. ramorum* from infected *V. tinus* roots was significantly reduced (P<0.05) when grown in Turface amended with *T. asperellum* demonstrating that *T. asperellum* can reduce secondary inoculum that is being release into the soil. Further, the percentage of roots colonized by *P. ramorum* was significantly lower (P<0.05) than the *T. asperellum*-amended Turface (24%) compared to the non-treated Turface (48%) confirming what was observed in *Viburnum tinus* root protection experiment above. Since the roots were inoculated before treatment with *T. asperellum*, this shows that the antagonist was able to reduce the spread within the root system or reduce infection on newly formed roots via secondary inoculum. Reduced infection lowers the amount of inoculum that may be released into the soil or waterway, thereby reducing the spread of this pathogen.

To date, *T. asperellum* has never been documented to be a plant pathogen on any host and is phylogenetically distant from the mushroom pathogen, *T. aggressivum* (Tondje et at, supra). In addition, it is incapable of growing at body temperature (37° C.) eliminating the possibility that it could be a pathogen of immune-compromised mammals.

The highly antagonistic isolates of *T. asperellum* are applied to the soil as a biocontrol composition comprising a highly antagonistic isolate of *T. asperellum* and an agriculturally acceptable carrier, wherein the agriculturally acceptable carrier is any one of autoclaved rice, autoclaved wheat bran, or other autoclaved grain that supports the growth of *T. asperellum*. The agriculturally acceptable carrier may further comprise a second biocontrol agent, an emulsifier, a nutrient, a wetting agent, or a substrate.

The highly antagonistic isolates of *T. asperellum* are applied to soil in amounts effective to reduce population levels of in the soil. As used herein "reduce population levels" refers to a reduction in numbers of *P. ramorum* propagules compared to that which would be expected in soil which was not treated according to the methods of the present invention. Any accurate method of measuring and comparing population levels may be used for such comparisons, as would be apparent to those skilled in the art.

As used herein "in amounts effective", "an amount effective" or "an effective amount" refer to the amount of colony forming units (CFU), comprised mainly but not solely of conidia of *T. asperellum* isolates, administered wherein the effect of the administration acts to reduce *P. ramorum* populations in the soil. The *T. asperellum* isolates are applied to the soil at a rate of approximately $1 \times 10^7$ CFU/cm$^3$ of soil.

As used herein "remediate" refers to the suppression of *P. ramorum* populations to non-detectable levels resulting in suppression of the spread of *P. ramorum*, thus alleviating the need for removal of large quantities of soil, repeated destruction of plants, and complete closure of nursery locations.

As used herein "protect" refers to that situation where potting soil free of *P. ramorum* and amended with *T. asperellum* 04-22 suppresses of the growth of *P. ramorum* populations when *P. ramorum* occur after potting soil has been treated or amended with *T. asperellum* 04-22 and thus preventing spread of *P. ramorum* populations.

EXAMPLES

Having now generally described this invention, the same will be better understood by reference to certain specific examples, which are included herein only to further illustrate the invention and are not intended to limit the scope of the invention as defined by the claims.

Example 1

Culture Isolates

All *Trichoderma* spp. isolates used in this study were received from Gary Samuels, Agricultural Research Service, United States Department of Agriculture, Beltsville, Md. The identifications and details are listed in Table 1. Isolates were maintained on half-strength potato dextrose agar (½PDA).

For soil tests, larger quantities of the selected *Trichoderma* spp. isolates were grown on twice autoclaved rice grains, first soaked in water, in sterile Erlenmeyer flasks at 20° C. for 10-14 days (Cavalcante et al. 2008. *Food Bioproc. Tech.* 1:100-104). The colonized rice was emptied into aluminum trays, air-dried for 3 days at room temperature, and ground into a coarse powder with a blender. The colony forming units (CFU) per g of colonized rice was measured by preparing several serial dilutions in 0.2% water agar and plating 1 ml of the final suspension onto each of 10 plates containing solidified *Trichoderma* Selective Medium (TSM; Askew and Laing. 1993. *Plant Path.* 42:686-690).

TABLE 1

Identification and characteristics of *Trichoderma* isolates.

| Isolate | Species | Geographic Location | Substratum |
|---|---|---|---|
| 01-15 | *T. asperellum* | Russia | Soil |
| 04-22 | *T. asperellum* | USA- Maryland | Soil |
| 01-294 | *T. asperellum* | Saudi Arabia | Soil |
| 04-92 | *T. asperellum* | Vietnam | Soil |
| 02-66 | *T. asperellum* | Cameroon | Soil |
| 02-65 | *T. asperellum* | Cameroon | Soil |
| 02-63 | *T. asperellum* | Cameroon | Soil |
| 02-64 | *T. asperellum* | Cameroon | Soil |
| 06-287 | *T. asperellum* | Nigeria | Soil |
| 06-283 | *T. asperellum* | Equador | *Cacao* flowers |
| 04-72 | *T. asperellum* | Italy | *Gypsophila*, stem |
| 07-66 | *T. asperellum* | Brazil | *Cacao* stem endophyte |
| 04-199 | *T. koningiopsis* | Peru | Soil |
| 04-40 | sp. nov. | Brazil | *Cacao* trunk endophyte |
| G2 | *T. virens* | USA-Oregon | *Phellinus* root |
| G3 | *T. virens* | USA-Oregon | *Phellinus* root |

Three different *P. ramorum* isolates, WSDA-1172, 5-C, both A2 mating type and clonal lineage NA1, and PrN-1 (CBS 101327), mating type A1 and clonal lineage EU1, were cultured on 20% clarified V8 agar. The isolates are maintained in liquid nitrogen for long term storage as part of the international collection of plant pathogens at the National Cancer Institute Central Repository, Frederick, Md.

Chlamydospores of *P. ramorum* isolate WSDA-1772 were produced by the method described by Mitchell and Kannwischer-Mitchell (1992. In: *Methods for Research on Soilborne Phytopathogenic Fungi*. Singleton et al. (Eds.). The American Phytopathological Society. St. Paul, Minn., pp. 31-38) and stored in autoclaved sand at 4° C. as described by Widmer et al. (1998. *Plant Dis.* 82:683-688). Five agar plugs (5-mm-diameter) containing actively growing mycelium of *P. ramorum* isolate WSDA-1772 were placed in 20 ml of 20% sterile, clarified V8 broth in sterile Petri plates (100-mm-diameter) and stored at 20° C. in the dark. After 4 weeks, the mycelia and chlamydospores were transferred to a blender cup containing 50 ml of sterile water and blended for 20 seconds. The suspension was mixed with autoclaved masonry sand and stored at 20° C. for at least 2 weeks until the mycelium was no longer viable. The concentration of the chlamydospores in the sand was measured by diluting 5 cm$^3$ of the infested sand in 95 ml of 0.2% water agar and plating 1 ml on *Phytophthora*-selective medium (PARPH+V8; Ferguson and Jeffers. 1999. *Plant Dis.* 83:1129-1136). The *P. ramorum* colonies were counted after 3 days and the chlamydospores concentration per cm$^3$ of sand was calculated based on the average over 10 plates. The sand inoculum was stored at 4° C. for long term storage until it was ready to be used.

Example 2

Dual Culture Bioassay

An agar plate bioassay was conducted as described by Krauss et al. (1998. *Biol. Control* 13:111-119). The *Trichoderma* spp. were grown on ½PDA in 90-mm-diameter Petri plates until they completely colonized the plate. A 1 cm by 4 cm strip of *Trichoderma*-colonized ½PDA was removed and transferred to a *P. ramorum*-colonized (isolate WSDA-1772) V8 agar plate. A non-colonized ½PDA strip was overlaid on a *P. ramorum*-colonized V8 agar plate as a control. Every week for 4 weeks a 1 cm by 4.5 cm strip perpendicular to the original *Trichoderma* strip, including the 1 cm portion beneath it, was removed. The strip was cut lengthwise in half and divided into 0.5 cm cubes to give two sets of nine cubes (FIG. 1). From one of the sets, the cubes were placed individually on the abaxial side of nine, wounded Rhododendron 'Cunningham's White' leaf disks (6-mm-diameter). The corresponding set was placed on a 20% V8 agar plate supplemented with 50 mg/l of benomyl (V8+B). After 1 week at 20° C., observations we made on the leaf disks for necrosis and P. ramorum mycelia growth originating from the cubes on the V8 agar plate. The experiment was conducted three times for each Trichoderma isolate.

To confirm that antagonistic activity was not specific for a particular isolate of P. ramorum, six Trichoderma isolates (02-64, G2, 06-283, 06-287, 02-65, and 04-22) were selected to repeat the test described above on two additional P. ramorum isolates (5-C and PRN-1). This test was conducted two times for each Trichoderma isolate against each P. ramorum isolate.

Figure 2:
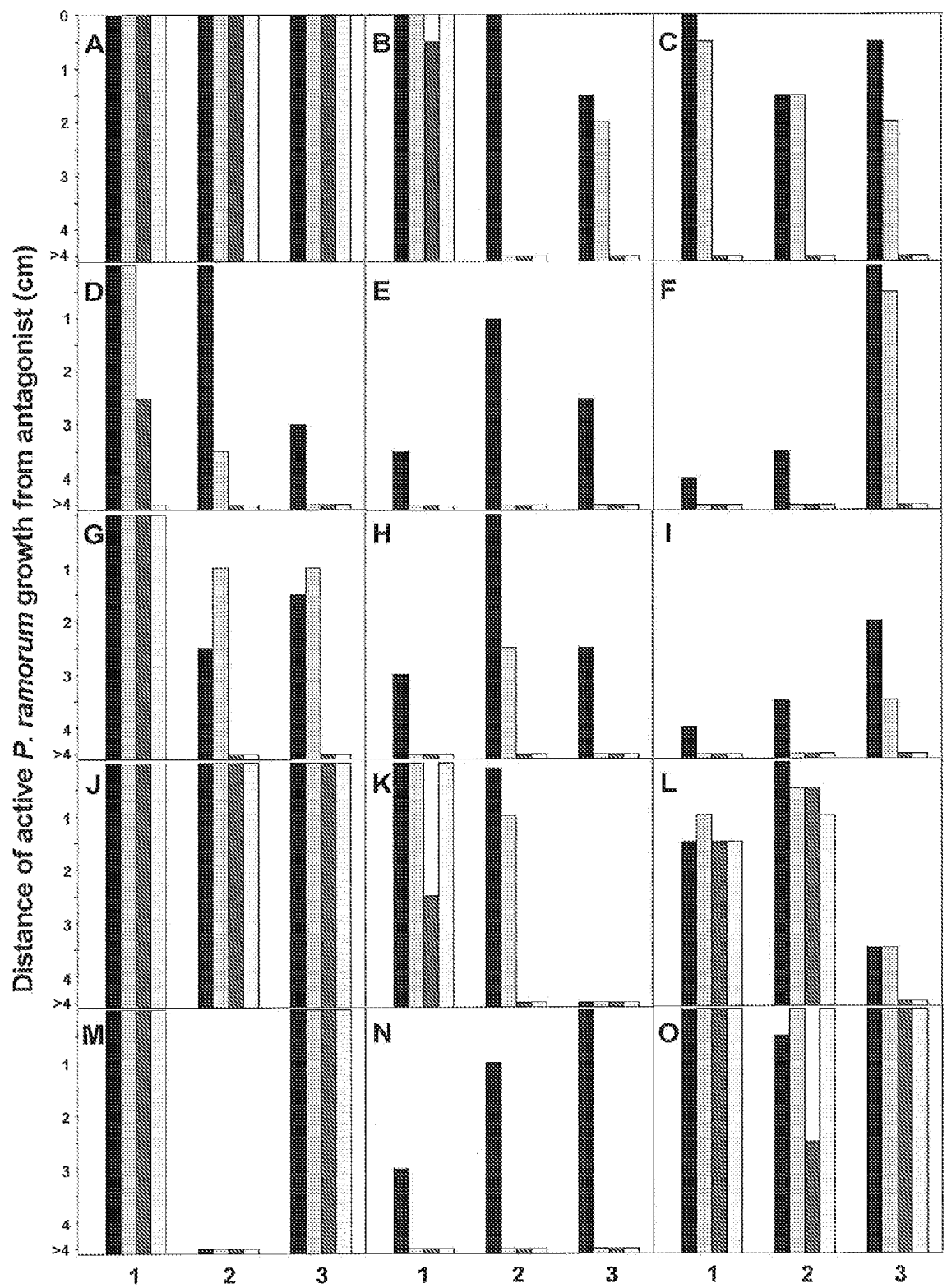
FIGS. 2A-2O depict the distance of *Phytophthora ramorum* WSDA-1772 growth from an overlaid strip of *Trichoderma* spp. isolate in the dual culture bioassay (Example 2) after 1, 2, 3, and 4 weeks (represented by bars from left to right) for three different repetitions (labeled 1, 2, 3 along X-axis). Distance of 0 cm is directly under overlaid antagonist strip and ">4" represents possible growth beyond the maximum distance measured. Control (A); Isolates: 02-66 (B), 07-66 (C), 04-22 (D), 06-287 (E), 01-294 (F), 01-15 (G), 06-283 (H), 02-64 (I), 02-63 (J), 04-40 (K), 04-72 (L), 04-199 (M), 02-65 (N), and 04-92 (O). Isolates G2 and G3 were similar to the control and are not shown.

Consistent antagonism of P. ramorum isolate WSDA-1772 over the three repetitions was observed for isolates 04-22 (FIG. 2D), 07-66 (FIG. 2C), 06-287 (FIG. 2E), 01-294 (FIG. 2F), 06-283 (FIG. 2H), 02-64 (FIG. 2I), and 02-65 (FIG. 2N). This was confirmed by both the lack of P. ramorum mycelia growth from the agar plugs and infection of rhododendron leaf disks exposed to the agar plugs. Tests conducted against P. ramorum isolates 5-C and PRN-1 showed no differences than what was observed with isolate WSDA-1772, confirming that the antagonism is not specific for a particular isolate. Although there was some inconsistency among the three different repetitions for some of the isolates, e.g. isolate 01-15 (G), which demonstrated the ability to eliminate growth in trials 2 and 3, but not in trial 1, the majority of the isolates chosen for further studies were consistent in all three trials. However, a few isolates that were inconsistent among the trials were also chosen for evaluation of whether there was a correlation between the dual culture and soil assays.

Figure 3:
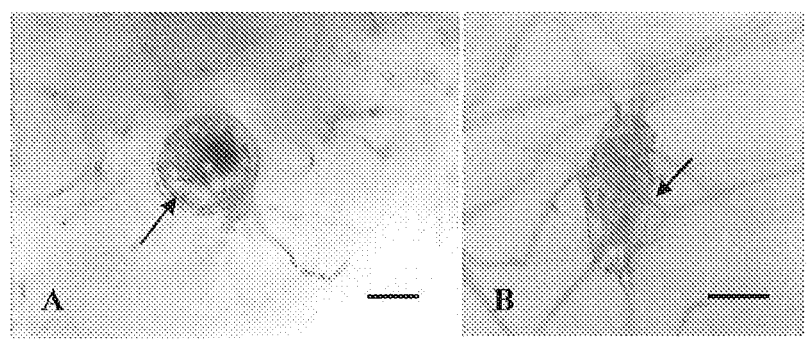
FIGS. 3A and 3B depict *Trichoderma asperellum* (arrows) demonstrating mycoparasitism of a *P. ramorum* chlamydospore (A) and sporangium (B). Bar=20 μm.
Figure 4:
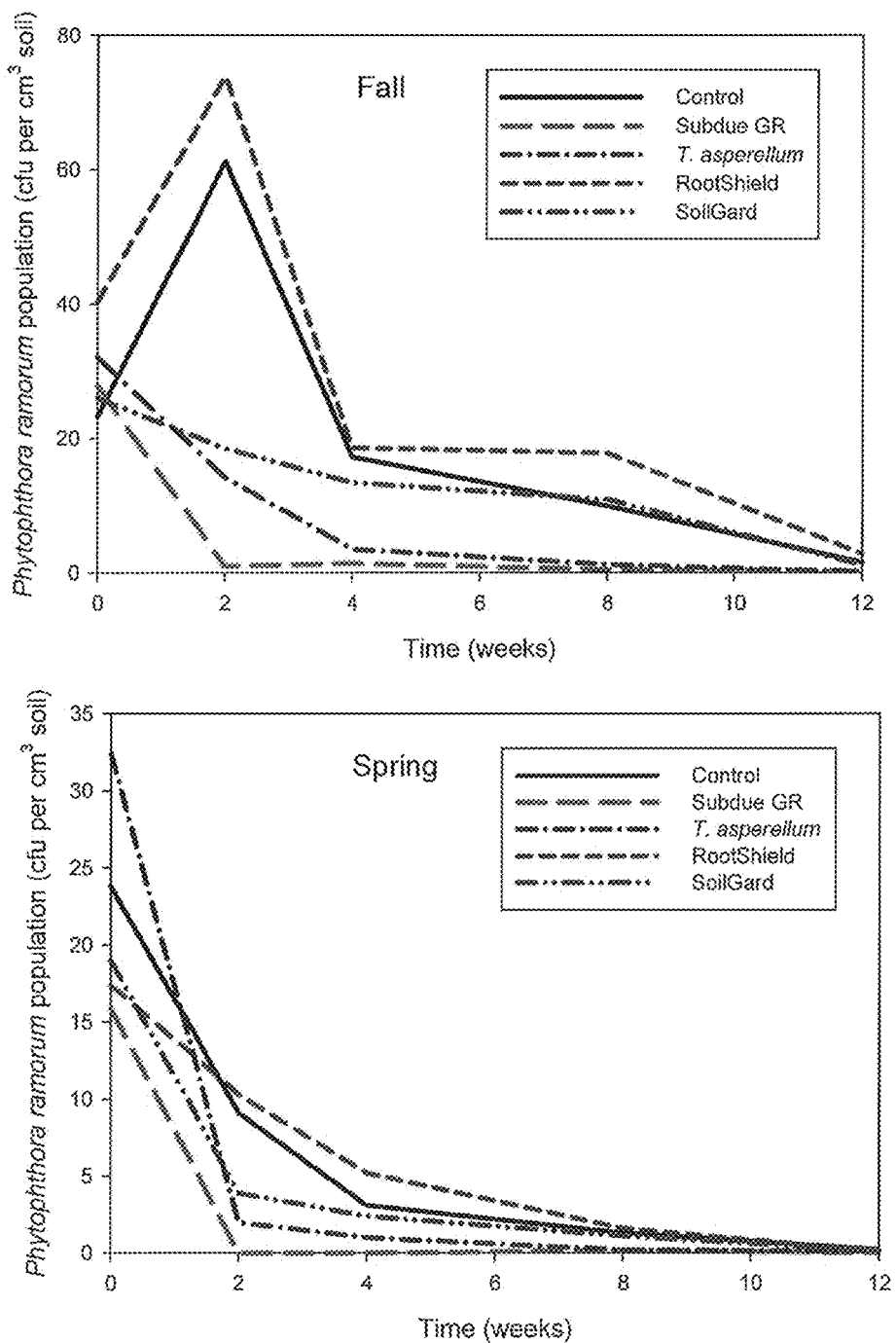
FIG. 4 shows soil populations ($CFU/cm^3$) of *Phytophthora ramorum* over time after treatment in Fall and Spring with *T. asperellum* isolate 04-22 grown on wheat bran (- ·· -; Green), RootShield® (----; Blue), SoilGard® (- ··· -; Maroon), Subdue GS® (——; Red) and Non-treated control (—; Black).
Figure 5:
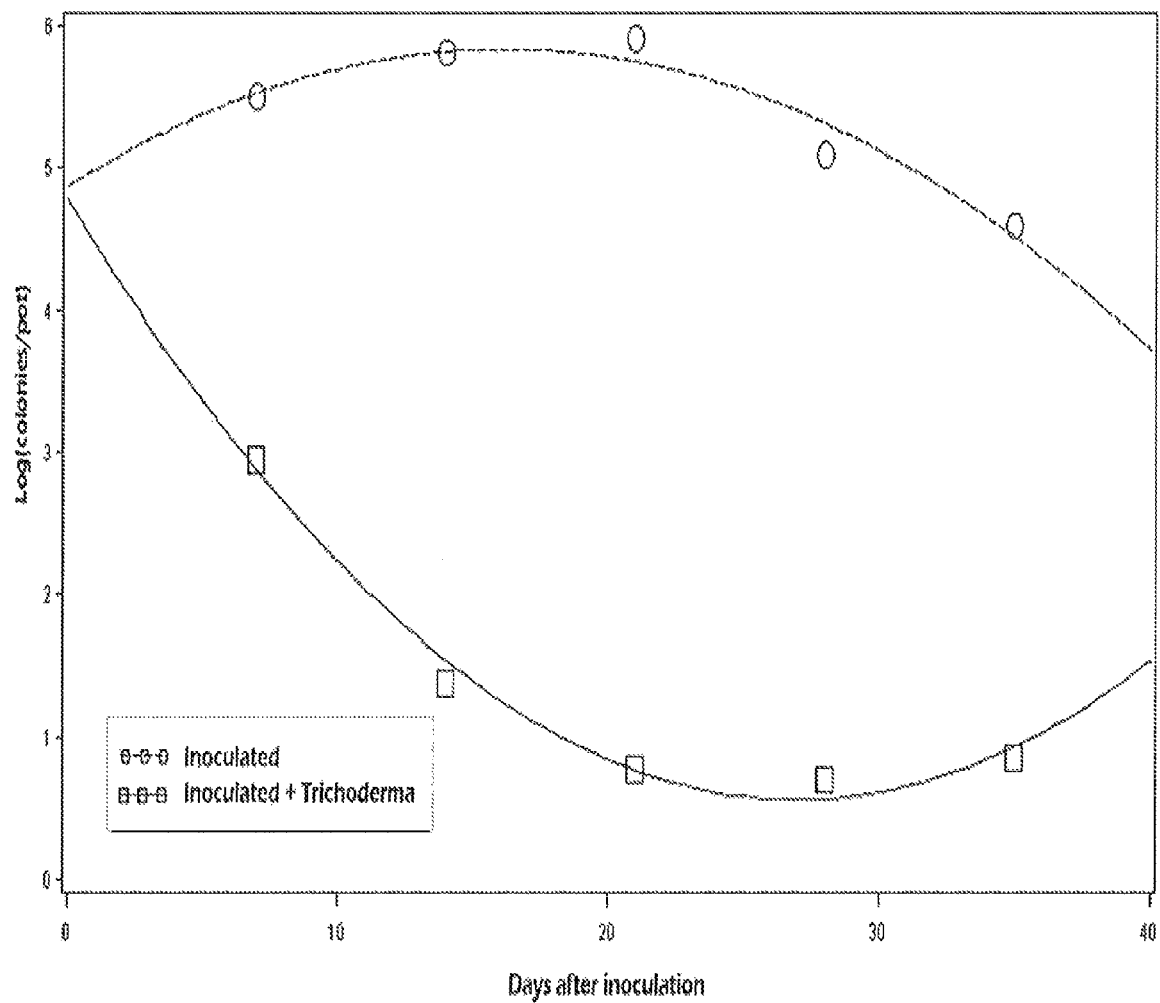
FIG. 5 shows a comparison of *P. ramorum* sporulation (expressed as Log of colonies of *P. ramorum* per pot) from infected *Vibumum tinus* roots grown over time in *T. asperellum*-amended Turface or non-amended Turface (○-inoculated with *P. ramorum*; □-inoculated with *P. ramorum+T. asperellum*).

Microscopic examination of the interaction between the antagonistic Trichoderma spp. and P. ramorum revealed mycoparasitism of P. ramorum chlamydospores and sporangia (FIG. 3).

Example 3

Soil Bioassay

Isolates 04-22, 06-287, 06-283, 01-294, 02-65, 02-64, 04-199, 07-66 and 02-66 were chosen for further testing using a soil bioassay. The Trichoderma spp. isolates were grown on the autoclaved rice and prepared as described above. An equal mixture of autoclaved potting mix (consisting of 41% peat, 11% bark, 23% perlite, 23% vermiculite, 2% sand, and a small amount of granular trace element blend) and masonry sand was dispensed into plastic bags, adjusted to 10% moisture, and infested with P. ramorum chlamydospores in sand, prepared as described above, to a final concentration of approximately 150 CFU/cm$^3$. Colonized rice was added to each of the bags so that the final concentration of the antagonist was $1\times10^7$ CFU/cm$^3$. Each week, an aliquot of each of the infested potting mix/sand treatments was removed, diluted in 0.2% water agar and plated on PARPH+V8 selective medium to monitor the changes in P. ramorum populations. The experiment was conducted two times for each of the antagonist isolates. Reduction of P. ramorum populations were compared over time against controls using repeated measures analysis in SAS for Windows version 9.2 (SAS, Institute, Cary, N.C.) after the data was log transformed for normality.

Soil bioassays demonstrated that isolates 02-64 and 04-22 significantly reduced ($P\leq0.05$) P. ramorum populations over time as compared to non-treated controls (Table 2). Other isolates, such as 06-287, 01-294, 07-66 and 02-65, reduced P. ramorum populations in one of the repetitions but overall were not different from the control. Production of the antagonist inoculum on rice and on such a small scale may be highly variable and may account for this inconsistency in antagonism in some of the isolates. It is significant to note that in some instances, populations of P. ramorum spiked dramatically after one week, mostly in the non-treated control soils, but also rarely in the antagonist-treated soils. This is most likely due to the rice being a very good substrate for P. ramorum, perhaps stimulating sporangia production and therefore zoospore release. However, in the presence of the antagonist, this proliferation of sporangia was limited. It appears that all of the isolates tested in the soil had some impact on limiting P. ramorum sporulation. Other substrates for growing the antagonist in order to optimize production and activity are needed. Possible substrates include: wheat bran (see Example 4), extracted conidia alone, and Biodac, a product composed of recycled cellulosic-based paper waste (Grantec, Inc., Granger, Ind.). Wheat bran is available, inexpensive, and has been demonstrated to be an effective substrate for other Trichoderma spp. (Cavalcante et al., supra). In addition, a wheat bran preparation of T. harzianum controlled Sclerotium rolfsii more efficiently than a conidial suspension of the same antagonist (Elad et al. 1980. Phytopath. 70:119-121). Biodac has also been demonstrated to be an effective substrate for other fungi used as biological control agents, including Trichoderma sp. (Mejia et al. 2008. Biol. Control 46:4-14.

TABLE 2

Statistical analysis of Trichoderma- vs. non-treatment.

| Isolate | P-value |
|---------|---------|
| 04-22   | 0.0024  |
| 02-64   | 0.0284  |
| 06-283  | 0.740   |
| 01-294  | 0.591   |
| 02-65   | 0.302   |
| 07-66   | 0.538   |
| 04-199  | 0.313   |
| 02-66   | 0.330   |
| 06-287  | 0.226   |

These results demonstrate that T. asperellum has the potential to eliminate soil populations of P. ramorum and further show that not all T. asperellum isolates have this ability. This information was the first step in developing T. asperellum as a biological control composition, i.e., agent, for remediation of soil infested with P. ramorum. Results of further testing for its validation as a biocontrol agent under natural nursery and field conditions are shown below.

Example 4

Field Studies

Trichoderma asperellum isolate 04-22, originally isolated from Maryland soil, was effective under laboratory conditions to reduce P. ramorum-infested medium as shown in Example 3. Isolate 04-22 was maintained on cornmeal agar at 20° C. for long-term storage. An agar piece containing mycelium was transferred to half-strength potato dextrose agar and allowed to grow for 5 days for immediate use. For large scale production, isolate 04-22 was grown on autoclaved wheat bran. A "seed" culture was first prepared by adding a plug (3-mm-diameter) of agar from the culture grown on half-strength potato dextrose agar containing active *T. asperellum* mycelium to 10 ml of half-strength potato dextrose broth. The culture was allowed to grow for 5 days at 20° C. Autoclaved wheat bran was prepared by mixing wheat bran (300 g) with water (300 ml) in spawn bags with a 0.2 μm filter (Fungi Perfecti, Olympia, Wash.) and autoclaving twice for 30 min at 121° C. on successive days. After the autoclaved wheat bran cooled, the "seed" culture was added to the autoclaved wheat bran, the bags were sealed by heat and the wheat bran and 04-22 culture were mixed well. The bags were then placed in a 20° C. incubator under continuous fluorescent lighting (3000 Lux) and incubated for 10 days. The bags were opened and the colonized wheat bran was air dried and pulverized in a blender to a consistency of a coarse powder. The CFUs per g of colonized wheat bran was determined by plating 1 ml of serial dilutions of colonized wheat bran in 0.2% water agar onto each of 10 plates containing solidified Trichoderma Selective Medium (Askew and Laing, supra). The colonized wheat bran was stored in plastic bags at 4° C. until tested (usually less than 2 weeks).

*Phytophthora ramorum* isolate PR-1, originally isolated from *Quercus agrifolia* in Marin County, Calif., and used previously in other studies (Harnick at al. 2004. *HortScience* 39:1677-1680; Swain et al. 2006. *J. Appl. Microbial.* 101: 815-827) was used as the inoculum source. Chlamydospores were produced following the methods described by Mitchell and Kannwischer-Mitchell (supra). The resulting mycelial-chlamydospore suspension was blended and added to autoclaved sand (10% moisture) and stored at 20° C. for at least 2 weeks and then at 4° C. until ready to use. Using this method results in an inoculum void of any other propagules except chlamydospores (Colburn and Shishkoff. 2006. *Phytopath.* 96:S25; Graham, J. H. 1990. *Plant Dis.* 74:743-746).

Study Site One: The National Ornamentals Research Site, Dominican University of California, San Rafael, Calif. (NORS-DUC), located in a *P. ramorum*-infested county, is a secure site that has been established to conduct research on *P. ramorum* under natural conditions that are normal for nursery production of ornamentals. To examine the impact of various treatments, the field study was structured in a completely randomized split-plot design, comprising microplots (Sari et al. 2006. *Plant Path. J.* 5:307-314; Shew and Beute. 1984. *Phytopath.* 74:530-535; Viaene and Abawi. 1998. *Plant Dis.* 82:945-952; Voland and Epstein. 1994. *Plant Dis.* 78:461-466; Widmer and Abawi. 1998. *J. Nematol.* 30:522). The experimental plot was prepared in a raised, rectangular box: 9.1 m (L)×3.7 m (W)×0.6 m (H), 33.7 m², divided into two sections with a plastic liner in the bottom. The box was filled with field soil described in Table 3 to a height of 0.34 m. Twenty fiberglass microplots (60 cm high and 0.61 m in diameter) were inserted into the soil in each plot, the top edge of each microplot cylinder being 10 cm above the soil line. Each microplot was randomly assigned one of the following treatments: (1) Non-treated control; (2) Subdue GR® (Mefenoxam, Syngenta Crop Protection, Inc., Greensboro, N.C.); (3) *Trichoderma asperellum* isolate 04-22 grown on wheat bran as described above; (4) RootShield® (*Trichoderma harzianum* strain T-22, BioWorks, Inc., Victor, N.Y.); and (5) SoilGard® (*Gliocladium virens* GL-21, Certis USA, Columbia, Md.). The experiment was conducted during the fall and the following spring since natural *P. ramorum* populations are normally at their highest level during these seasons (Davidson et al., supra).

TABLE 3

Description of soil characteristics used in Field Trials.

| Study Site[a] | pH | C:N Ratio | % OM[b] | Total CEC[c] | Soluble Salts[d] | Composition (sand:silt:clay) | USDA Classification |
|---|---|---|---|---|---|---|---|
| Soil 1 | 5.8 | 279 | 5.9 | 23.6 | 1.33 | 41.1:35.6:23.3 | Gravelly loam |
| Soil 2 | 6.4 | 365 | 3.1 | 14.6 | 0.51 | 56.1:22.6:21.3 | Gravelly sandy clay loam |
| Soil 3 | 6.5 | 320 | 11.6 | 27.3 | 1.85 | 82.7:9.4:7.9 | Extremely gravelly loamy sand |

[a]Soil 1: used in Study Site One for the Fall 2010, Spring 2011, and Fall 2011 trials. Soil 2: used in Study Site One for the Spring 2012 trial. Soil 3: used in Study Site Two.
[b]Percent organic matter.
[c]Total cation exchange capacity (meq/100 g soil).
[d]Soluble salts (mmhos/cm).

In the fall, the soil within each microplot was artificially infested with an amount of the *P. ramorum*-infested sand, prepared as described above, so that the intended initial population of *P. ramorum* was approximately 30 propagules/cm³. Currently, the sizes of the *P. ramorum* populations present in naturally-infested nurseries and the threshold levels required for disease occurrence have not been determined. However, Sandler et al. (1989, *Plant Dis.* 73:902-906) showed that, for citrus, *P. nicotianae* populations should be approximately 10-15 propagules/cm³ of soil before treatments should be applied. Therefore, an initial population of *P. ramorum* at 30 propagules/cm³ was chosen so as to exceed that guideline. Soil infestation was done by evenly distributing an aliquot of *P. ramorum* chlamydospores-infested sand over the soil and raking it in to a depth of 3 to 5 cm. The plot was watered to settle the surface. After a one week period to allow for stabilization of the *P. ramorum* population, ten soil samples, approximately 5 cm deep and having a volume of approximately 20 cm³, were collected within each microplot in randomized areas throughout the microplot. The subsamples from each microplot were combined and stored in a plastic bag at 4-10° C. until sampled for *P. ramorum* and *Trichoderma* spp. populations.

Each microplot was treated with the designated treatment described below. For the chemical treatment microplots, 6.64 g of Subdue® GR was applied as a broadcast at the recommended rate (22.9 g per m² of soil surface0. Although not specifically used as a soil remediation agent in the past, Subdue® GR has been shown to be effective as a soil drench in reducing lesion size caused by *Phytophthora* spp. (Benson and Blazich. 1989. *J. Environ. Hort.* 7:73-75; Linderman and Davis, 2008b, supra). A preliminary laboratory study showed that Subdue Maxx® (Syngenta Crop Protection Inc., Greensboro, N.C.) applied as a drench to *P. ramorum*-infested soil reduced the soil population to non-detectable limits when it was assayed two days later (Widmer, unpublished). For the *T. asperellum*, RootShield® and SoilGard® treatments, the formulated products were weighed to their recommended rates. RootShield® and SoilGard® were applied at 6.12 g (concentration of $1\times10^7$ CFU/g product) and 14.2 g (concentration of $1\times10^6$ CFU/g product) per microplot, respectively. For the *T. asperellum* isolate, formulated as described above, the weight added per microplot depended upon the concentration of *T. asperellum* per gram of wheat bran of the individually prepared batch. The intended final concentration of *T. asperellum* was of $1\times10^7$ CFU per $cm^3$ of soil to a depth of 2 cm. The *T. asperellum*, RootShield® and SoilGard® treatments were added to each microplot as evenly as possible and raked into the soil to a depth of 2 cm. The microplots were hand watered to settle the soil as per the recommendation on the Subdue® GR label.

After 2, 4, 8 and 12 weeks, ten soil subsamples were taken from each microplot and combined in the same manner as described above for prior to the applied treatments. The combined samples were sent by overnight delivery to Fort Detrick, Md. and stored at 4° C. until they were processed the next day as described below. After the last samples were taken at 12 weeks, the microplots and the soil were disinfected with steam via a steam generator. The plot was prepared and established again for the spring trial as described above. The experiment was repeated the following year.

*P. ramorum* soil populations of the microplots were quantified by the soil dilution plating method. The combined subsamples from each microplot were mixed thoroughly and two 10-$cm^3$ samples were removed and added to 80 $cm^3$ of 0.2% water agar slurry. The suspensions were thoroughly mixed with a wrist-action shaker for approximately 10 min. One milliliter of the soil slurry was removed and plated onto the *Phytophthora*-selective medium, PARPH+V8 (Ferguson and Jeffers, supra), 10 plates per sample. The soil suspension was evenly distributed on the agar and incubated in the dark at 20° C. After 3 days, the soil was washed off the plates and the *P. ramorum* colonies were counted and confirmed as *P. ramorum* based upon morphological characteristics (Werres et al. 2001. *Mycolog. Res.* 105:1155-1165).

*Trichoderma* spp. soil populations were quantified by the soil dilution plating method. From the original soil dilution used above, further dilutions were prepared in 0.2% water agar slurry, depending upon the expected outcome. One milliliter of the final dilution was plated on *Trichoderma* Selective Medium, five plates per sample. Colonies identified as *Trichoderma* spp. were counted after one week.

After the completion of the 2-year study, data were combined, separating the fall and spring results. The data were analyzed by SAS version 9.2 (SAS Institute, Cary, N.C.) by PROC MIXED using repeated measures analysis.

Differences were noted in the *P. ramorum* population pattern when the fall and spring trials were compared; therefore, they were analyzed separately (FIG. 4). In the fall applications, *P. ramorum* populations increased in the non-treated control and RootShield®-treated microplots after 2 weeks and then declined over time, although always maintaining a detectable level up to the final sampling time of 12 weeks. The *P. ramorum* population in the chemical-treated microplots immediately fell to non-detectable levels, but was detected again in some of the individual microplots after 4 and 8 weeks. Populations of *P. ramorum* in the *T. asperellum*- and SoilGard®-treated microplots started to decline immediately. *P. ramorum* was not detected after 8 weeks in the *T. asperellum*-treated microplots and remained at non-detectable levels up to the last sampling time. *P. ramorum* was detected in some of the microplots treated with SoilGard®, although some had non-detectable levels. In the spring application, *P. ramorum* populations immediately declined in all treatments. However, after 8 and 12 weeks, *P. ramorum* populations were not detectable only in the *T. asperellum*- and chemical-treated microplots. Other treatment groups returned to detectable levels.

Declines in *P. ramorum* populations, even in the non-treated control microplots, is not surprising due to the poor saprophytic behavior of *Phytophthora* spp. in general (Erwin and Ribeiro, supra). Since there was no plant material in the microplots for the *P. ramorum* to colonize, an increase or maintenance of its population would not be expected. Decline in populations over time collected from soil has been observed in other studies and may be seasonal (Davidson at al., supra; Tooley at al. 2008. *Plant Dis.* 92:431-437). However, populations may again recover later. An initial increase in *P. ramorum* population in the fall application of the control and RootShield®-treated microplots may reflect conditions that were conducive to germination and sporulation of the chlamydospores, which gave a temporary increase in population due to the release of zoospores.

Despite the decline in *P. ramorum* populations over time in the non-treated control microplots, statistical differences were noted in the *T. asperellum* and chemical treatments as compared to the control treatments at some sampling times in both the fall and spring trials (Table 4). However, no differences were found at any of the sample times between the soil treated with RootShield® or SoilGard® and the controls. This may reflect differences in the main mode of action and intended application between these two commercial products and the experimental *T. asperellum*. Although multiple modes of action are suggested for RootShield® and SoilGard® on the product labels, it appears that the main ones are competitive exclusion and production of an antibiotic compound based upon claims that they are not eradicants, but protectants. Therefore, it would be assumed that these products are more effective in protecting a host plant from infection in the presence of the pathogen. This is in contrast to *T. asperellum*, which appears to have mycoparasitism as the main mode of action (Watanabe at al., supra; Widmer and Samuels, supra) and, therefore, is effective even if the pathogen is present before treatment.

TABLE 4

Significance of Treatments[a] compared to non-treated controls on *P. ramorum*.

| | FALL | | | | SPRING | | | |
|---|---|---|---|---|---|---|---|---|
| Time Weeks | 04-22 | Root-Shield ® | Soil-Gard ® | Subdue ® | 04-22 | Root-Shieid ® | Soil-Gard ® | Subdue ® |
| 0 | NS[b] | NS | NS | NS | NS | NS | NS | NS |
| 2 | * | NS | NS | * | * | NS | NS | * |
| 4 | * | NS | NS | * | * | NS | NS | * |

TABLE 4-continued Significance of Treatments[a] compared to non-treated controls on *P. ramorum*.

| | FALL | | | | SPRING | | | |
|---|---|---|---|---|---|---|---|---|
| Time Weeks | 04-22 | Root-Shield ® | Soil-Gard ® | Subdue ® | 04-22 | Root-Shieid ® | Soil-Gard ® | Subdue ® |
| 8 | * | NS | NS | * | * | NS | NS | * |
| 12 | * | NS | NS | * | NS | NS | NS | NS |

[a]Treatments: *Trichoderma asperellum* isolate 04-22 grown on wheat bran; commercial product RootShield ®, commercial product SoilGard ®, and application of Subdue GS ® fungicide.
[b]Statistical analysis using repeated measures analysis comparing treatments with non-treated controls (Not Significant: NS, P > 0.05; Significant: *, P ≤ 0.05)

*Trichoderma* species were detected in all soils prior to the treatments. These species have not been identified to date so their impact on *P. ramorum* is not known. However, since the soil was uniformly distributed throughout the main plot, one would expect that any effect would be equal in all microplots. In the RootShield®-, SoilGard®- and *T. asperellum*-treated microplots, populations of *Trichoderma* spp. ranged between 10 and 100 times higher than the non-treated controls and chemical-treated microplots. These populations remained fairly steady through the last sampling time after 12 weeks from application.

Study Site Two: A commercial nursery in the San Joaquin Valley, Calif. that had tested positive for *P. ramorum* in the soil from samples collected by State Regulators. Soil type was a heavily compacted, extremely gravelly, loamy sand (Table I). Plot size set for treatment was 3.7 m by 4.6 m. Due to the heavy compaction of the soil, half of the plot was rototilled to a depth of 2 cm. Wheat bran colonized by *T. asperellum*, described above, was distributed as evenly as possible over the entire plot. The total amount of *T. asperellum* added to the plot was $6.74 \times 10^{11}$ CFU, which was 2600 g of wheat bran. The wheat bran was raked into the soil to an approximate depth of 1 to 2 cm. The soil was initially hand watered to settle the plot and watered when necessary by overhead irrigation to maintain moisture in the soil. Another plot, 3.5 by 4 m in size, and approximately 15 m from the treated plot, was left untreated as a control and maintained as described above.

Soil samples were collected from six locations throughout the treated (half were in the rototilled section) and non-treated plot prior to the application of the colonized wheat bran and 5 weeks after application. The samples were processed by adding approximately 20 cm$^3$ of the soil to 50 ml of 0.1 mM MES buffer, pH 6.2 in a 270 ml plastic cup (8.5-cm-diameter). After the soil had settled, five *Rhododendron* 'Cunningham's White' leaf disks (11-mm-diameter) were placed abaxial-side down on the liquid surface. The cups were loosely covered to reduce evaporation and placed in an incubator at 20° C. in the dark.

After one week, the leaf disks were removed, surface sterilized in 70% ethanol for 20 sec, rinsed three times in sterile water, and plated on PARPH+V8 selective medium. The plates were examined after 5 days and plugs containing mycelium growing from the leaf disks were individually transferred to clarified V8 agar for identification. *Phytophthora ramorum* was identified based upon morphological characteristics (Werres of al., supra). Once *P. ramorum* was not detected in the baited samples processed above from the treated plot, it was requested to the California Department of Food and Agriculture (CDFA), Plant Health and Pest Prevention Services officials to collect and process samples according to their official protocols.

At study site two, *P. ramorum* was detected in the soil prior to the treatment. Five weeks after the application of *T. asperellum*, *P. ramorum* was not detected in the collected soil samples from the treated plot, regardless of whether the plot was rototilled or not. These results were confirmed when officials from CDFA collected their samples one week later and processed them according to their official regulatory guidelines that included analyzing the material by PCR techniques. As a result of these negative findings, USDA/APHIS-PPQ released the nursery from quarantine status.

In conclusion, results in this study demonstrate that *T. asperellum* could remediate soil infested with *P. ramorum* under natural field conditions. These results also show that the experimental *T. asperellum* is more effective than two commercially-available biological control products, thereby confirming the need to develop this species as a new commercially-available product.

Example 5

Protection of Plant Roots from Infection by *P. ramorum*

*P. ramorum* isolates WSDA-1772 and 5-C were maintained on 20% clarified V8 agar at 20° C. Sporangia of both *P. ramorum* isolates were produced as described by Widmer (Widmer, T. L. 2010. *Plant Health Progress* doi:10.1094/PHP-2010-0317-01-RS). Cultures of *P. ramorum* were grown by transferring three plugs from the edge of an actively growing culture of each isolate in 6 ml of 10% clarified V8 broth in 60-mm-diameter Petri plates. The cultures were incubated at 20° C. under continuous light (3000 Lux). After 5 days, the sporangia were separated from the mycelium by vigorously shaking the cultures and filtering through four layers of sterile cheesecloth. Afterwards, approximately 5 ml of sterile 10% V8 broth was added to the mycelium, shaken vigorously and filtered through the cheesecloth to combine the suspensions. The sporangia concentration per ml was calculated by averaging the number of sporangia in three 20-µL drops and multiplying by fifty.

Chlamydospores of *P. ramorum* isolate WSDA-1772 were produced by the method described in Example 1, i.e., the methods of Mitchell and Kannwischer-Mitchell (1992) and Widmer et al. (1998). Chlamydospores were extracted from the sand by mixing 20 cm$^3$ of the infested sand with 50 cm$^3$ of sterile water and shaking vigorously for 5 seconds. Immediately after the sand settled, the suspension was filtered through a 63 µm screen into a beaker. The concentration of the chlamydospores in the filtrate was calculated by averaging the number of sporangia in three 20-µL drops and multiplying by fifty.

Cuttings of *Viburnum tinus* 'Compactum' (syn. 'Spring Bouquet') were produced by dipping the stem end in Hormodin 2 (OHP, Inc., Mainland, Pa.; active ingredient Indole-3-butyric Acid 00.3%) and then planting in either Fafard 52 potting mix (Conrad Fafard, Inc., Agawam, Mass.) or Turface MVP (a calcined, montmorillonite clay substrate medium manufactured by Profile Products LLC, Buffalo Grove, Ill.). Cuttings were kept under a mist tent for 5 to 10 weeks, until adventitious roots with lateral root development were present.

Potting mix (consisting of 41% peat, 11% bark, 23% perlite, 23% vermiculite, 2% sand, and a small amount of granular trace element blend) was dispensed into four plastic bags, 3 L aliquots per bag. The potting mix in three bags was amended with *T. asperellum*, isolate 04-22, grown on wheat bran as described in Example 3 and the field studies of Example 4, so that the final concentrations were $1\times10^5$, $1\times10^6$, and $1\times10^7$, CFU/cm$^3$ of potting mix in bags 1, 2, and 3, respectively. The fourth bag was left non-amended as a control. The potting mix, adjusted to 10% moisture by adding 300 nil water, was mixed well and stored at 20° C. for 1 week before being used as described below.

Twenty-four rooted *V. tinus* cuttings grown as described above were selected based on uniformity of root growth. The cuttings were transplanted into square plastic pots, 8.5 cm diameter, (SVD-350-BK-450; T.O. Plastics, Clearwater, Minn.) containing approximately 300 cm$^3$ of the amended or non-amended potting mix prepared above. The pots were placed on a greenhouse bench with drip irrigation. One week later, the *V. tinus* cuttings were inoculated with *P. ramorum* by drenching the soil in each pot with a 25-ml suspension of either 9500 chlamydospores (approximately 32 per cm$^3$ potting mix) or 56,000 sporangia (approximately 120 per cm$^3$ potting mix). The pots were maintained on the greenhouse bench with drip irrigation for 3 weeks.

Afterwards, the cuttings were removed from the soil and the stem cut at the soil line. The roots were surface-sterilized in 70% ethanol, rinsed three times in sterile water, and plated onto the *Phytophthora*-selective medium, PARPH+V8 (Ferguson and Jeffers, 1999). The roots were observed for *P. ramorum* mycelium growth into the agar medium after 1 week and noted as positive if any *P. ramorum* growth was observed. The experiment was conducted a total of two times.

Results clearly showed that *T. asperellum* affords some protection of the roots from infection of *P. ramorum*. In the non-amended potting soil control group, 75% of the plants showed some infection of *P. ramorum* on the roots. However, as the concentrations of *T. asperellum* increased, a correlation with root protection was observed. At the $10^5$, $10^6$, and $10^7$ concentrations, only 42%, 33%, and 25% of the plants in the *T. asperellum*-amended potting mix showed infection, respectively. Thus, preventing infection of the roots of plants planted in potting soil is not only beneficial to the individual plant but the decrease in *P. ramorum* infection also helps to diminish the spread of *P. ramorum* infestation into the environment.

There was no difference between chlamydospore or sporangia infestation so all data were combined for this analysis. This relationship between antagonist inoculum dose and the level of infection is important in evaluating the efficacy of the biological control agent and its eventual commercialization as a consumer product.

Example 6

Suppression of Sporulation of *P. ramorum* on Plant Roots

*V. tinus* plants were tested for inoculum production on roots using an assay developed to quantify *P. ramorum* inoculum in runoff (Shishkoff, supra). Twelve plants transplanted in Turface were inoculated by pouring 50 ml of a sporangial suspension (500 sporangia/ml) over each root system established in approximately 80 ml of Turface and allowing 24 hr for infection. Four control plants were treated with water alone. Plants were then removed from the infested or noninfested (control) Turface and the roots carefully washed to remove all Turface granules (and any residual inoculum from infested plants). Plants were then transplanted into 50×20 mm plastic pots containing approximately 100 ml of clean Turface. The bottom of each pot was lined with plastic mesh (pore size ca. 0.5 mm) for easy drainage. After inoculation, plants were kept in a controlled-environment chamber set at 20° C. with a 14-hr photoperiod. Three days after transplanting, six of the inoculated plants and two of the controls were treated with a top-dressing of wheat bran infested with *T. asperellum*. The amount of bran added was calculated to deliver a dose of $1\times10^7$ spores/cm$^3$ of Turface. Each treatment had its own plastic tray so that runoff from one treatment did not have an opportunity to contact plants from another treatment. Trays from a given experiment were placed in the same growth chamber, but were moved randomly to different positions within the growth chamber at each sampling time. Runoff was sampled at 7, 14, 21, 28 and 35 days after inoculation. Sampling consisted of pouring enough distilled water through the pot to collect 20 to 25 ml of runoff into a plastic centrifuge tube. Runoff was sub-sampled using a plastic syringe to add 1 ml aliquots to each of three plates of P$_5$ARPH. Plates were swirled to distribute a film of runoff over the entire surface, and then incubated at 20° C. Plates were examined weekly for 3 weeks and all colonies counted using a dissecting microscope with dark-field illumination (under which colonies of *P. ramorum* are characteristically highly refractive) in order to quantify the colony-forming units per ml of runoff. At the end of the experiment, roots were washed and then surface-sterilized for 30 sec in 0.025% sodium hypochlorite, rinsed in distilled water for 30 min, and then 1-cm segments plated on P$_5$ARPH selective medium. Ideally, 80 root segments per plant were plated. After a 2-week incubation at 20° C., colonies from plated roots were counted to determine percent infection.

Inoculum in runoff over time for infected roots was analyzed after "colonies per pot" was transformed using a logarithmic (base e) transformation with "0" values replaced by "1" to retain low counts on the log scale. The transformed variable was analyzed by random coefficient analysis using mixed model analysis of covariance program (to take into account that the same plants were sampled over time). Pairwise treatment differences were compared using the least significant difference (LSD) at each sampling time. The amount of inoculum produced by each plant could be totaled for the entire experimental time period to get "total colonies per pot" for each plant. This was analyzed by general linear models (GLM) in SAS and treatment means compared using LSD to test the treatment differences. Percent root colonization at the end of the experiment was analyzed by GLM after performing an arcsin square root transformation to normalize data and treatments were compared by using LSD to test the treatment differences.

Sporulation of *P. ramorum* from infected *V. tinus* roots was also significantly reduced (P<0.05) when grown in Turface amended with *T. asperellum* (FIG. 1). This is important since it demonstrates that *T. asperellum* can reduce secondary inoculum that is being release into the soil. In addition, the percentage of roots colonized by *P. ramorum* in this experiment was significantly lower (P<0.05) than the *T. asperellum*-amended Turface (24%) compared to the non-treated Turface (48%) confirming what was observed in Example 5 described above. Since the roots were inoculated before treatment with *T. asperellum*, this shows that the antagonist was able to reduce the spread within the root system or reduce infection on newly formed roots via secondary inoculum. A brief study showed that not only did *T. asperellum* grow on the root surface, but it also grew as an endophyte in the root (unpublished data). More work is needed to determine what effect *T. asperellum* as an endophyte might play in protection of the root system.

These results are significant because they demonstrate that *T. asperellum* can protect plant roots from infection when inoculated with *P. ramorum* propagules. This reduction in infection will lower the amount of inoculum that may be released into the soil or waterway, thereby reducing the spread of this pathogen.

Deposit of the Microorganisms: *Trichoderma asperellum*, isolate 04-22, designated NRRL50844 has been deposited under the provisions of the Budapest Treaty on Jun. 18, 2013 with the U.S.D.A. Agricultural Research Service Patent Culture Collection (National Center for Agricultural Utilization Research, 1815 N. University Street, Peoria, Ill., 61604).

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A biocontrol agent comprising:

a) a biologically pure culture of an antagonistic microorganism effective 1) for the suppression of growth and spread of *Phytophthora ramorum*, 2) for the remediation of soil infected with *P. ramorum* and 3) for protecting plant roots from infection by *Phytophthora ramorum* wherein the antagonistic microorganism is the *Trichoderma asperellum* isolate 04-22 (NRRL 50844), and b) an agriculturally acceptable carrier, wherein the carrier is any one of autoclaved rice, autoclaved wheat bran, or other autoclaved grain that supports the growth of *T. asperellum*.

2. The biocontrol composition according to claim 1 wherein said composition further comprises one or more biocontrol agents in addition to *T. asperellum* isolate 04-22 (NRRL 50844), an emulsifier, a nutrient, a wetting agent, or a support.

3. The biocontrol agent of claim 1 wherein said agent is prepared by a process comprising:

(a) inoculating said autoclaved grain with the *T. asperellum* culture of claim 1, (b) allowing said culture to grow to increase the population of *T. asperellum,*

(c) air drying grain colonized with *T. asperellum*, and (d) determining the CFUs per g of colonized grain as a measure of colonization by the inoculant isolate.

4. A biocontrol agent wherein said agent is prepared by a process consisting essentially of:

(a) preparing a suspension of autoclaved wheat bran in spawn bags, (b) preparing starter cultures of the antagonistic *T. asperellum* isolate 04-22 (NRRL 50844), (c) inoculating said autoclaved wheat bran in said spawn bag with the antagonistic *T. asperellum* 04-22 (NRRL 50844) culture, sealing said spawn bag, and mixing to form a wheat bran—*T. asperellum* culture, (d) placing said spawn bag containing the wheat bran—*T. asperellum* culture in a 20° C. incubator under continuous fluorescent lighting (3000 Lux) and incubated for 10 days, (e) air drying the colonized wheat bran and then pulverizing to the consistency of coarse powder, (f) determining the CFUs per g of colonized wheat bran as a measure of colonization by the inoculant isolate, and (g) adjusting the concentration CFUs/g to obtain a desired dosage of CFUs/g of the biocontrol agent comprising *T. asperellum* isolate-colonized wheat bran.

5. A method for reducing *Phytophthora ramorum* populations in the soil comprising:

(a) applying the biocontrol agent of claim 1 to treat the soil in an amount sufficient to reduce *P. ramorum* populations in the soil, (b) removing an aliquot from treated soil and from untreated control soil at particular periods of time, (c) diluting the aliquots in 0.2% water agar and plating on PARPH+V8 (pimaricin, ampicillin, rifampicin, pentachloronitrobenzene, hymexazol plus V8 juice) selective medium to monitor the changes in *P. ramorum* populations at each particular period of time, (d) comparing populations of *P. ramorum* populations from treated soil and from untreated control soil over time, and (e) determining an amount that is effective to reduce *P. ramorum* populations in said soil.

6. A method for remediating *Phytophthora ramorum*-infested soil comprising:

(a) inoculating soil containing *P. ramorum* with the biocontrol agent of claim 1 in an amount sufficient to reduce *P. ramorum* populations in the soil, (b) removing an aliquot from treated soil and from untreated control soil at particular periods of time, (c) diluting the aliquots in 0.2% water agar and plating on PARPH+V8 selective medium to monitor the changes in *P. ramorum* populations at each particular period of time, (d) comparing populations of *P. ramorum* populations from treated soil and from untreated control soil over time, and (e) obtaining the result where *P. ramorum* is no longer detectable in said soil after treatment with said biocontrol agent.

7. A method for protecting plant roots from infection by *Phytophthora ramorum* comprising:

(a) amending potting soil with the biocontrol agent of claim 1 so that the final concentration is at least $1\times10^5$ CFU/cm$^3$, (b) transplanting rooted cuttings into said amended potting soil, and (c) observing a decrease in *P. ramorum* infection when soil from plants potted in amended soil is compared to plants potted in untreated soil.

8. A method for suppression sporulation of *P. ramorum* on plant roots comprising:

(a) top-dressing the root system of transplanted plants with the biocontrol agent of claim 1 so that the final concentration is at least $1\times10^5$ CFU/cm$^3$, (b) sampling runoff from growing plants periodically in order to monitor for infestation with *P. ramorum*, wherein for said sampling distilled water is poured through a potted plant to collect runoff for determining presence of *P. ramorum* on selective medium, and (c) observing a decrease in *P. ramorum* infection when runoff from plants treated with a top-dressing of the biocontrol agent of claim 1 is compared to untreated plants.

* * * * *